United States Patent
Mobley et al.

(10) Patent No.: US 7,287,617 B2
(45) Date of Patent: *Oct. 30, 2007

(54) VEHICLE IGNITION INTERLOCK SYSTEMS WITH MULTIPLE ALCOHOL SENSORS

(75) Inventors: Larry J. Mobley, Raleigh, NC (US); Brian McMillin, Willoughby Hills, OH (US); Jimmy H. Edwards, Wake Forest, NC (US); James R. Lewis, Raleigh, NC (US)

(73) Assignee: Monitech, Inc., Morrisville, NC (US)

( * ) Notice: Subject to any disclaimer, the term of this patent is extended or adjusted under 35 U.S.C. 154(b) by 361 days.

This patent is subject to a terminal disclaimer.

(21) Appl. No.: 11/113,778

(22) Filed: Apr. 25, 2005

(65) Prior Publication Data

US 2006/0237254 A1    Oct. 26, 2006

(51) Int. Cl.
*B60K 28/06* (2006.01)

(52) U.S. Cl. .............. 180/272; 340/576; 600/532; 180/279

(58) Field of Classification Search .......... 180/272, 180/279, 271, 735; 340/576, 573.1, 561, 340/522; 73/233; 436/132, 900; 600/532; 422/84; 307/10.1

See application file for complete search history.

(56) References Cited

U.S. PATENT DOCUMENTS

| | | |
|---|---|---|
| 3,780,311 A | 12/1973 | Brown |
| 3,824,537 A | 7/1974 | Albertson |
| 3,831,707 A | 8/1974 | Takeuchi |
| 4,093,945 A | 6/1978 | Collier et al. |
| 4,592,443 A | 6/1986 | Simon |
| 4,697,666 A * | 10/1987 | Collier et al. ............... 180/272 |
| 4,738,333 A | 4/1988 | Collier et al. |

(Continued)

FOREIGN PATENT DOCUMENTS

WO    WO 97/27561    7/1997

(Continued)

OTHER PUBLICATIONS

International Search Report and Written Opinion for International Application No. PCT/US2006/015440, mailed Feb. 14, 2007.

(Continued)

*Primary Examiner*—Paul N. Dickson
*Assistant Examiner*—Tiffany L. Webb
(74) *Attorney, Agent, or Firm*—Myers Bigel Sibley & Sajovec, P.A.

(57) ABSTRACT

A vehicle ignition interlock system includes a breath analyzer and a controller operably connected to the breath analyzer and to an ignition system of the vehicle. The breath analyzer detects breath alcohol level of a vehicle operator and prevents vehicle ignition if a breath alcohol level is greater than or equal to a threshold value. The controller requires the vehicle operator to periodically take breath analyzer "retests" after vehicle ignition in order to allow vehicle operation to continue. The breath analyzer includes first and second alcohol sensors. The second alcohol sensor is a backup for the first alcohol sensor and becomes operational if the first alcohol sensor malfunctions. The first or second alcohol sensors may be a mouth contamination sensor that distinguishes between mouth contaminants and alcohol contained within a deep lung breath sample. The system also includes sensors configured to detect impact (abuse) and vehicle motion.

34 Claims, 2 Drawing Sheets

U.S. PATENT DOCUMENTS

| | | | |
|---|---|---|---|
| 4,770,026 A | 9/1988 | Wolf | |
| 4,901,058 A | 2/1990 | Comeau | |
| 4,902,628 A | 2/1990 | Blair | |
| 4,912,458 A | 3/1990 | Comeau et al. | |
| 4,926,164 A | 5/1990 | Porter et al. | |
| 5,020,628 A | 6/1991 | Bigliardi et al. | |
| 5,048,321 A | 9/1991 | Chow | |
| 5,393,495 A | 2/1995 | Forrester | |
| 5,531,225 A * | 7/1996 | Nawata et al. | 600/532 |
| 6,026,674 A * | 2/2000 | Gammenthaler | 73/19.01 |
| 6,229,908 B1 | 5/2001 | Edmonds, III et al. | |
| 6,625,527 B1 | 9/2003 | Ding et al. | |
| 2002/0084130 A1 | 7/2002 | Der Ghazarian et al. | |
| 2002/0089660 A1 | 7/2002 | Weiss | |
| 2002/0127145 A1 | 9/2002 | Der Ghazarian et al. | |
| 2003/0036823 A1 | 2/2003 | Mahvi | |
| 2003/0117287 A1 | 6/2003 | Crespo | |
| 2003/0176803 A1 * | 9/2003 | Gollar | 600/532 |
| 2003/0183437 A1 | 10/2003 | Mendoza | |
| 2003/0209893 A1 * | 11/2003 | Breed et al. | 280/735 |
| 2004/0050718 A1 | 3/2004 | Traylor, III | |
| 2004/0138823 A1 | 7/2004 | Gollar | |
| 2004/0158430 A1 | 8/2004 | Ballard, Jr. et al. | |
| 2004/0236199 A1 | 11/2004 | Hawthorne et al. | |

FOREIGN PATENT DOCUMENTS

WO     WO 02/058962 A1     8/2002

OTHER PUBLICATIONS

Annex to Form PCT/ISA/206 Communication Relating to the Results of the Partial International Search for PCT/US2006/015440; Date of mailing Sep. 27, 2006.

* cited by examiner

VEHICLE IGNITION INTERLOCK SYSTEMS WITH MULTIPLE ALCOHOL SENSORS

FIELD OF THE INVENTION

The present invention relates generally to sobriety testing devices and, more particularly, to vehicle ignition interlock systems.

BACKGROUND OF THE INVENTION

Vehicle operation by persons under the influence of alcohol is a well known safety problem in the United States and throughout the world. Thousands of deaths per year in the United States are attributable to drivers operating vehicles under the influence of alcohol. To address this problem, most states have established laws that prohibit operation of a vehicle by an individual with a blood alcohol content (BAC) greater than a preset value (e.g., 0.08% BAC). In addition, "ignition interlock" systems have been developed which are directly connected to a vehicle's ignition system and are designed to prevent vehicle operation by inebriated individuals. Many states require the installation of ignition interlock systems in the vehicles of individuals convicted of driving under the influence of alcohol, particularly repeat offenders.

Conventional ignition interlock systems include a breath analyzer which measures the alcohol content of the breath of an individual. It is well known that the alcohol content of gas present in the alveoli of the lungs has an alcohol content directly proportional to that of the bloodstream of an individual. Blood alcohol content, thus, can be accurately determined by measuring breath alcohol content with a breath analyzer.

Typically, in order to start a vehicle equipped with an ignition interlock system, the driver must first blow into the breath analyzer. If the driver's breath alcohol exceeds a preset limit, the vehicle's ignition is disabled and the vehicle is rendered inoperable. If the driver's breath alcohol is below the preset limit, ignition is permitted and the vehicle may be started. If a driver successfully passes an initial breath test and is allowed to start a vehicle, some ignition interlock systems will require one or more retests (typically random) of the driver after vehicle ignition. These retests may occur as the driver is operating the vehicle (referred to as "rolling retests") or the driver may be required to stop the vehicle prior to taking the retest. If the driver either refuses to take a retest or if the driver's breath alcohol exceeds a preset limit, vehicle operation may be disabled or may become disabled within a preset period of time. Exemplary ignition interlock devices that utilize breath analyzers are described in, for example, U.S. Pat. Nos.: 3,780,311; 3,824,537; 3,831,707; and 4,592,443.

Operation of conventional ignition interlock systems is unsupervised. This lack of supervision has led to various attempts to bypass the breath analyzer such as by using air or other gases from balloons, bicycle pumps, gas station air hoses, and other sources. As a result, conventional ignition interlock systems may include breath temperature and humidity detection sensors to deter the use of non-human breath samples.

The lack of supervision has also led to attempts by vehicle operators to circumvent ignition interlock devices by using breath samples of non-driving individuals. To deter a person other than a vehicle operator from taking a breath test in order to start a vehicle, conventional ignition interlock systems have utilized various ways for confirming the identity of the person providing the breath sample. For example, the use of retina scans, voice identification, and face recognition have all been utilized. See, for example, U.S. Patent Application Publication Nos.: 2002/0089660, 2002/0084130 and 2002/0117287. Unfortunately, many of these systems are complicated and expensive.

Accordingly, there exists a need for a cost effective and reliable ignition interlock system that is capable of discriminating, without human supervision, between a vehicle operator and other persons in order to prevent circumvention of the ignition interlock system.

SUMMARY OF THE INVENTION

In view of the above discussion, a vehicle ignition interlock system, according to embodiments of the present invention, includes a breath analyzer located within a vehicle and a controller that is operably connected to the breath analyzer and to an ignition system of the vehicle. The breath analyzer is configured to detect the breath alcohol level of an operator of the vehicle. The controller compares detected breath alcohol levels of the vehicle operator with a threshold value, and is configured to prevent vehicle ignition (i.e., prevent the vehicle from being started) if a breath alcohol level detected by the breath analyzer is greater than or equal to a threshold value. The controller is configured to require the vehicle operator to periodically take breath analyzer "retests" after vehicle ignition in order to allow vehicle operation to continue.

The breath analyzer includes first and second alcohol sensors, each configured to detect breath alcohol levels of an operator of the vehicle. The second alcohol sensor is a backup for the first alcohol sensor and becomes operational if the first alcohol sensor malfunctions. The first and second alcohol sensors may be the same type of alcohol sensor or may be different types. Exemplary types of alcohol sensors that can be used in accordance with embodiments of the present invention include, but are not limited to, electrochemical fuel cells, infrared sensors, and metal oxide semiconductor sensors.

According to embodiments of the present invention, at least one of the first and second alcohol sensors may be a mouth contamination sensor that is configured to distinguish between contaminants (e.g., mouthwash, cough syrup, other medications, etc.) in the mouth of a vehicle operator and alcohol contained within a deep lung breath sample. According to embodiments of the present invention, the controller may require a breath alcohol retest of the vehicle operator via the breath analyzer in response to detecting the presence of a contaminant within the mouth of the vehicle operator.

According to embodiments of the present invention, an operator identification device (e.g., a fingerprint identification device, hum-tone device, voice print device, face recognition device, PIN device, etc.) is operably connected to the controller and is configured to verify the identity of the vehicle operator via the operator identification device.

According to other embodiments of the present invention, the ignition interlock system includes a user selectable option that allows an individual to perform a breath alcohol test via the breath analyzer without enabling the vehicle ignition system. As such, the individual can use the ignition interlock system as a "personal", stand-alone breath analyzer.

According to other embodiments of the present invention, the vehicle ignition interlock includes a user interface that is operably connected to the controller and that is configured to display operational messages. The controller may also provide audible operational messages and prompts via the user interface, including voice messages in one or more languages.

According to embodiments of the present invention, a vehicle ignition interlock system may also include an impact sensor that is physically attached to one or more portions of the vehicle ignition interlock system. The impact sensor is configured to detect impact events experienced by the vehicle ignition interlock system as a result of, for example, abuse by an individual. The vehicle ignition interlock system controller is configured to record impact events detected by the impact sensor and to provide a message (e.g., a warning) to the vehicle operator in response to the impact sensor detecting an impact event. The impact sensor may be an accelerometer or other device capable of detecting impacts.

According to embodiments of the present invention, a vehicle ignition interlock system may include a motion detector configured to detect movement of the vehicle. Exemplary motion detectors that may be used in accordance with embodiments of the present invention include, but are not limited to, Global Positioning System (GPS) receivers, accelerometers, gyroscopic motion detectors, etc. The vehicle ignition interlock system controller can monitor movement of the vehicle via the motion detector and may be configured to provide a message to the vehicle operator in response to detecting movement of the vehicle and if the breath alcohol level of the operator has not been measured prior to the vehicle being set into motion when a vehicle start was not allowed. In addition, where the motion detector is a GPS device, the controller may also log vehicle geographic locations periodically and/or when breath analyzer tests and/or retests are required. This would be useful in programs where a user's driving privileges were restricted to certain geographic regions, such as only being allowed to drive between work and home, etc.

DETAILED DESCRIPTION OF THE INVENTION

The present invention now is described more fully hereinafter with reference to the accompanying drawing, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "on" another element, it can be directly on the other element or intervening elements may also be present. In contrast, when an element is referred to as being "directly on" another element, there are no intervening elements present. It will be understood that when an element is referred to as being "connected" or "attached" to another element, it can be directly connected or attached to the other element or intervening elements may also be present. In contrast, when an element is referred to as being "directly connected" or "directly attached" to another element, there are no intervening elements present. The terms "upwardly", "downwardly", "vertical", "horizontal" and the like are used herein for the purpose of explanation only.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. All publications, patent applications, patents, and other references mentioned herein are incorporated herein by reference in their entirety. As used herein, the term "and/or" includes any and all combinations of one or more of the associated listed items.

Figure 1:
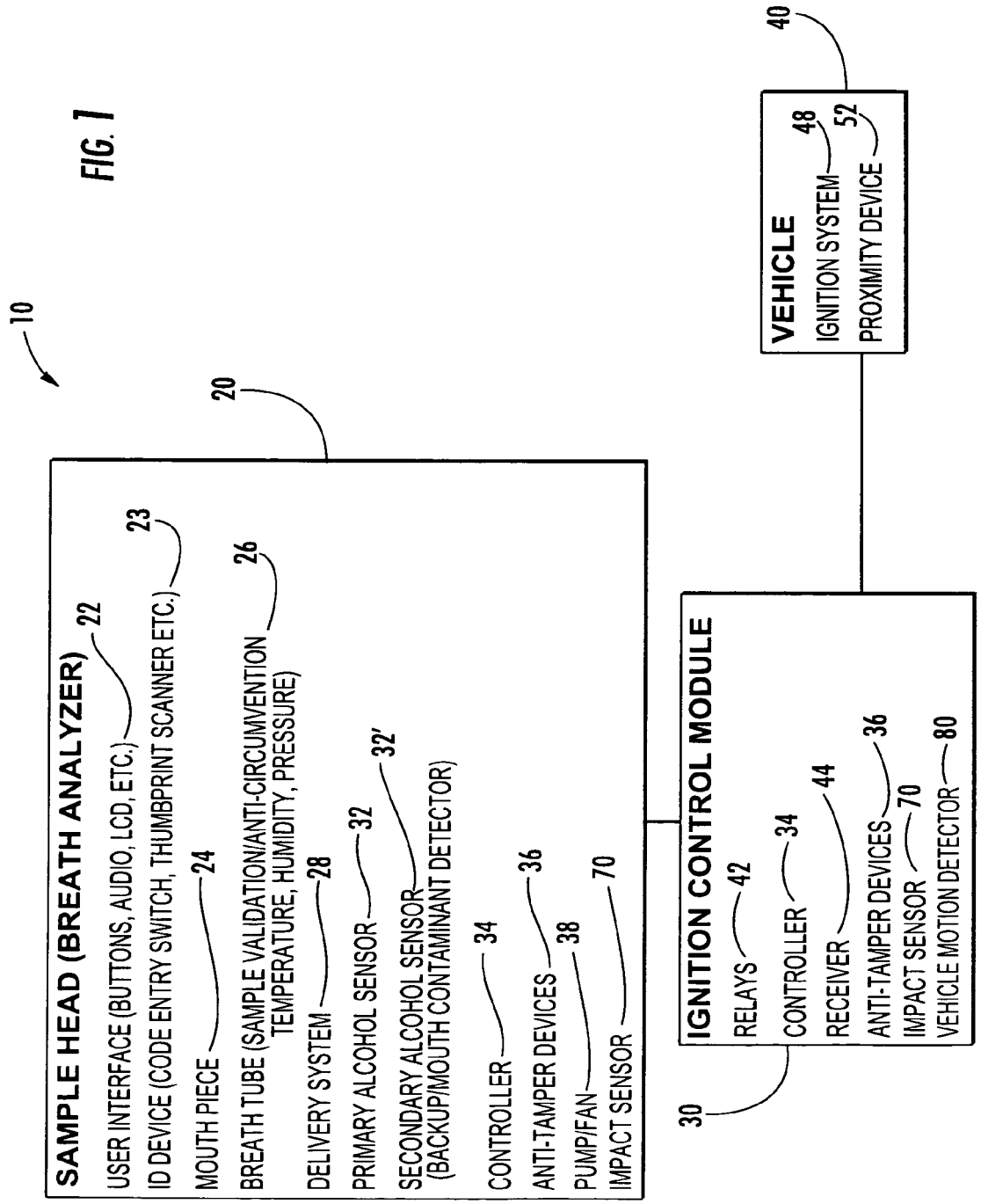
FIG. 1 is a block diagram that illustrates an ignition interlock system, according to embodiments of the present invention.

Referring now to FIG. 1, a vehicle ignition interlock system 10, according to embodiments of the present invention, is illustrated. The illustrated system 10 includes a sample head 20 that serves the function of a breath analyzer that is configured to measure breath alcohol levels of an operator of a vehicle 40. The terms "sample head" and "breath analyzer" are synonymous as used herein and are intended to be interchangeable. Exemplary sample head devices and their operation are described in U.S. Pat. Nos.: 4,093,945; 4,902,628; and 4,901,058.

The sample head 20 is operably attached to an ignition control module 30. The ignition control module 30 may be operably attached to various components of a vehicle's ignition and electronics system 48, which may include, but is not limited to, the battery, vehicle starter switch, tachometer, starter solenoid, etc. The ignition control module 30 may be operably connected to various vehicle systems/components, without limitation, to prevent starting and operation of the vehicle if the vehicle operator fails a breath alcohol test, as would be understood by those skilled in the art. The ignition control module 30 includes a controller 34, which preferably includes a processor and/or other suitable programmable or non-programmable circuitry, including suitable software. The controller 34 may also include other devices as appropriate to control various devices described herein. The controller 34 may be one or more processors or circuitry designed to implement the various functions described herein. Moreover, the functions of the controller 34 may be performed by circuitry or processor(s) located within the various components of the ignition interlock system 10 described herein.

The sample head 20 is located within a vehicle 40 and is typically in a convenient location for use by an operator of the vehicle. Preferably, the sample head 20 is a handheld apparatus that can be easily handled by a vehicle operator prior to and during vehicle operation. According to embodiments of the present invention, the sample head 20 includes a user interface 22 that is operably connected to the controller 34 and that is configured to display and/or perform operational messages in any of a number of formats. This includes messages in one or more languages on a text display (e.g., Liquid Crystal Display) and/or audible operational messages and prompts, including voice messages in one or more languages. At various times, instructions and prompts can be provided to the vehicle operator via the sample head 20 regarding when the next breath alcohol content retest is required, system status, etc. This can make vehicle operation safer, as the vehicle operator does not always need to actually look at the user interface 22 while driving. The user interface 22 may also include one or more push-button switches that the operator can depress to respond to various conditions or requests from the system 10, including the need to enter operator identification information (e.g., an entry code number or a thumbprint scan).

According to embodiments of the present invention, the sample head 20 includes a mouthpiece 24, which is used by the vehicle operator to blow a breath sample (e.g., a "deep lung" breath sample) into one or more alcohol sensors 32 in the sample head 20. The mouthpiece 24 communicates with the alcohol sensor(s) 32 via a breath tube 26 and a delivery system 28 (solenoid, syringe, etc.) that delivers a portion of a breath sample to the alcohol sensor(s) 32 for analysis. A deep lung breath sample is an expiratory sample of alveolar air (i.e., air from the alveolar region of the lungs) which is known to have an alcohol concentration proportional to blood alcohol concentration of an individual. According to embodiments of the present invention, the sample head 20 may also include various features in the breath tube 26 that are configured to thwart circumvention by a vehicle operator, such as breath temperature sensors, breath humidity sensors, pressure sensors, etc., as would be understood by those skilled in the art.

The controller 34 is configured to compare detected breath alcohol levels of a vehicle operator with a threshold value, and to prevent vehicle ignition (e.g., by opening a circuit in the vehicle ignition system, etc.) if a breath alcohol level of the vehicle operator, as measured by the sample head 20, is greater than or equal to the threshold value (e.g., 0.08% breath alcohol content, etc.). The term "prevent vehicle ignition" is intended to mean preventing a vehicle from being started, according to embodiments of the present invention. How a vehicle is prevented from being started may be accomplished in any of various ways known to those skilled in the art, and all of such ways are intended to be included within the scope of the present invention.

The ignition control module 30 contains relays 42 that are operably attached to a vehicle's ignition system 48. The relays 42 are actuated by the controller 34 to open or close a circuit in the vehicle ignition system 48. As would be understood by those skilled in the art, the circuit enables the ignition system 48 to start the engine of the vehicle 40.

If vehicle ignition is allowed (i.e., the breath alcohol level of the vehicle operator is below the threshold value) the controller 34 periodically requires the vehicle operator to take a breath alcohol content retest in order to allow vehicle operation to continue. The retesting periodicity preferably is random, but can also be regular. A retest may be a "running" retest wherein the vehicle operator can continue to drive the vehicle 40, or have the vehicle 40 "stand" while running, and blow a breath sample into the sample head 20. A retest may also be an "engine off" test where the operator stops the vehicle 40 and turns off the engine prior to blowing a sample into the sample head 20.

According to embodiments of the present invention, both the sample head 20 and the control module 30 have the capability to detect and log data into memory that may include system performance and conditions, conditions and results related to breath alcohol tests, functions of the vehicle, and possible evidence of system tampering or circumvention as detected by various anti-tamper devices (sensors) 36 in the system 10.

According to embodiments of the present invention, the sample head 20 includes a primary alcohol sensor 32 and a secondary alcohol sensor 32'. The primary and secondary alcohol sensors 32, 32' may be the same type of alcohol sensor or may be different types of alcohol sensors. Exemplary types of alcohol sensors that can be used in accordance with embodiments of the present invention include, but are not limited to, electro-chemical fuel cells, infrared sensors, and metal oxide semiconductor sensors. Exemplary fuel cells are available from Draeger USA, Inc., Durango, Colo. Exemplary infrared sensors are available from Cal Sensors, Inc. (e.g., lead selenide and lead sulfide detectors) Santa Rosa, Calif, and Electro Optical Components, Inc., (e.g., pyroelectric and thermopile detectors) Santa Rosa, Calif. Exemplary semiconductor sensors, (e.g., a Taguchi sensor), are available from Figaro USA, Inc., Glenview, Ill.

The primary and secondary alcohol sensors 32, 32' may be any of the following combinations of alcohol sensors, respectively: fuel cell—fuel cell; fuel cell—infrared; fuel cell—metal oxide semiconductor; infrared—fuel cell; infrared—infrared; infrared—metal oxide semiconductor; metal oxide semiconductor—fuel cell; metal oxide semiconductor—infrared; metal oxide semiconductor—metal oxide semiconductor, etc. Fuel cell technology, infrared technology and metal oxide semiconductor technology for use in detecting breath alcohol is well known in the art, and need not be described further herein.

The primary and secondary alcohol sensors 32, 32' may be interchangeable function-wise, or may each serve different functions. For example, both the primary and secondary alcohol sensors 32, 32' may be configured to detect alcohol within a breath sample of an individual. Thus, the primary and secondary alcohol sensors 32, 32' effectively may be interchangeable, with the secondary alcohol sensor 32' serving as a backup to the primary alcohol sensor 32. Thus, if the primary alcohol sensor 32 fails, the secondary alcohol sensor 32' serves the functions of the primary alcohol sensor 32.

According to embodiments of the present invention, either or both of the primary and secondary alcohol sensors 32, 32' may serve the function of a mouth contamination sensor that is configured to distinguish between contaminants (e.g., mouthwash, cough syrup, other medications, etc.) in the mouth of a vehicle operator and alcohol contained within a deep lung breath sample of the vehicle operator. Various substances in the mouth of a vehicle operator may give false readings to an alcohol sensor 32, 32'. For example, mouthwash, which often contains alcohol, may result in alcohol being detected in the breath of a vehicle operator by an alcohol sensor 32, 32'. However, because the alcohol is not from a deep lung breath of the operator, the operator may not be inebriated. A mouth contamination sensor, according to embodiments of the present invention, is capable of detecting whether the alcohol in the breath is from a deep lung sample or from a contaminant in the mouth. As used herein, the term "contaminant" is intended to include any and all possible substances an individual may have in his/her mouth including, but not limited to, mouthwash, medications, tobacco products, smoke, etc.

Figure 2:
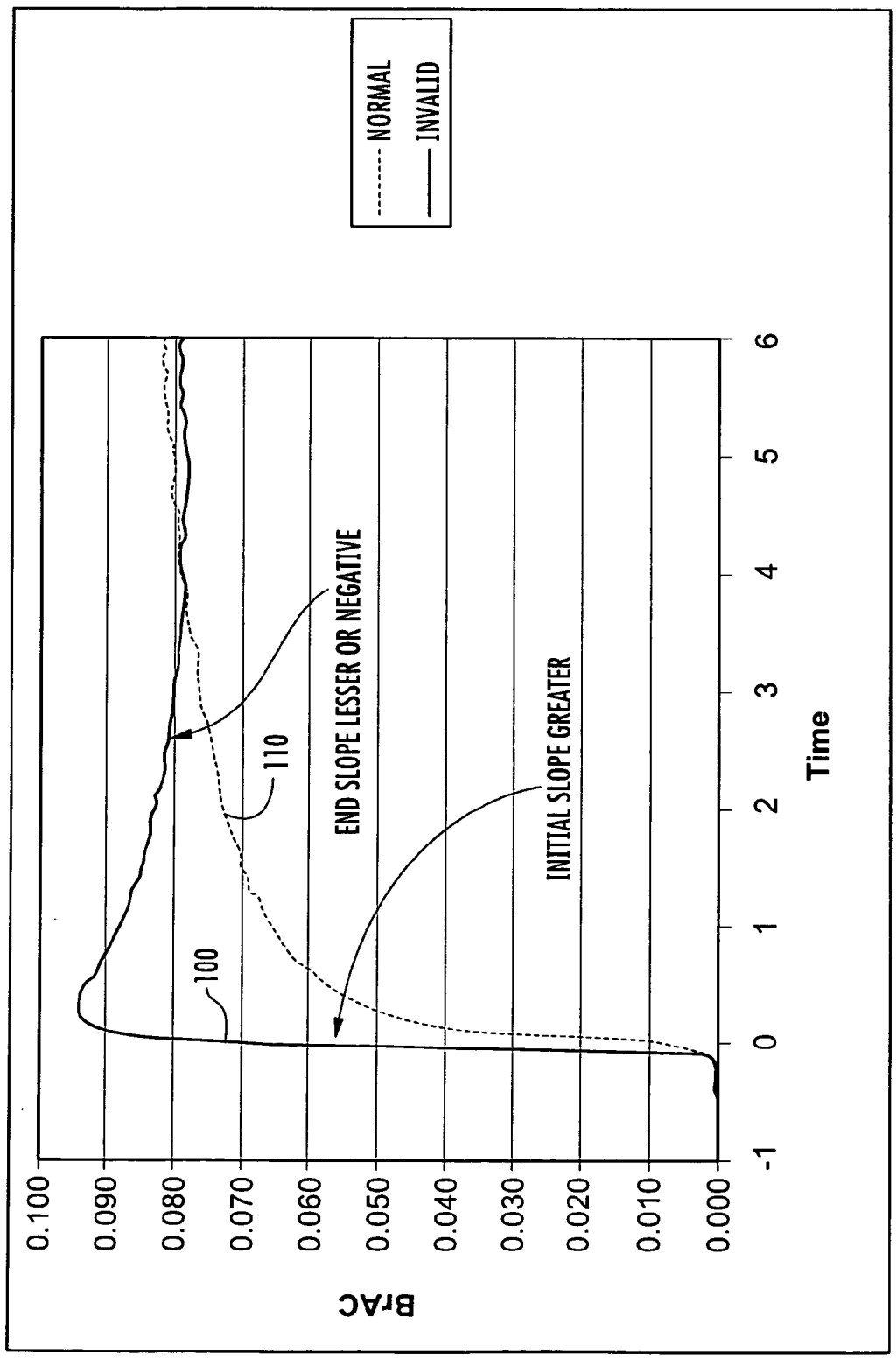
FIG. 2 is a graph that illustrates breath alcohol content versus time and which can be used to distinguish between alcohol in the mouth of a person and alcohol in a deep lung breath sample of a person.

An alcohol sensor 32, 32', when serving the function of a mouth contamination sensor, generates a real time alcohol level in response to receiving a breath sample. This data is converted into a curve plotted on a graph, and an algorithm is applied to it to analyze the characteristics of the curve. Referring to FIG. 2, a curve 100 with a slope that peaks quickly, and then decreases indicates that the alcohol level was highest from the breath that was in the individual's mouth; whereas, a true deep lung breath alcohol sample has an alcohol level that rises slower, but then stays nearly level for an extended time period (curve 110, FIG. 2). The sustained presence of alcohol from the breath sample indicates that the alcohol is originating from the lungs.

A mouth contamination sensor is not intended to override a primary alcohol sensor into allowing a vehicle to be started. A mouth contamination sensor is intended to indicate that an initial fail or warn level of a primary alcohol sensor may be the result of something other than a blood alcohol concentration.

According to embodiments of the present invention, the controller 34 may require a breath alcohol retest of the vehicle operator via the sample head 20 in response to detecting the presence of a contaminant within the mouth of the vehicle operator.

According to embodiments of the present invention, an operator identification device 23 (e.g., a fingerprint identification device, hum-tone device, voice print device, face recognition device, PIN entry device, etc.) is operably connected to the controller 34 and is configured to verify the identity of the vehicle operator via the operator identification device 23. The operator identification device 23 is configured to ensure that the vehicle operator is the one taking the breath alcohol tests and operating the vehicle 40. According to other embodiments of the present invention, the operator identification device 23 may be an input device that is configured to receive input (e.g., a PIN code) from a user. Failure to verify the identity of the vehicle operator can prevent the vehicle 40 from being started and operated. Some number of retry attempts may be allowed, as would be understood by those skilled in the art. Moreover, failure to verify the identity of the vehicle operator may result in a lockout period that prevents further attempts from being made, as would be understood by those skilled in the art.

According to embodiments of the present invention, the vehicle ignition interlock system 10 may also include a user selectable menu option that instructs the controller 34 to disable the vehicle ignition system and to allow an individual to perform a "personal inquiry" breath alcohol content test via the sample head 20. Accordingly, an individual can utilize the ignition interlock system 10 as a personal, stand-alone breathalyzer; however, the vehicle cannot be started or operated in this mode.

It is known that vehicle operators sometimes try to disable vehicle ignition interlock systems by hitting them with objects and/or by hurling them against objects. Thus, according to embodiments of the present invention, the vehicle ignition interlock system 10 may also include an impact sensor 70 that is physically attached to one or more portions of the vehicle ignition interlock system 10 (i.e., the breath analyzer 20 and/or ignition control unit 30). The impact sensor 70 is configured to detect impact events experienced by the breath analyzer 20 and/or ignition control unit 30 as a result of abuse by an individual. The controller 34 is configured to record impact events detected by the impact sensor 70.

According to embodiments of the present invention, the controller 34 is configured to provide a message (e.g., a warning) to the vehicle operator in response to the impact sensor 70 detecting an impact event. Such messages may be visual messages and/or audio messages, and may be provided via user interface 22. For example, an audio message may be a voice message in one or more languages.

The impact sensor 70 may be an accelerometer or other device capable of detecting impacts. Accelerometers are well known and need not be described further herein.

According to embodiments of the present invention, the vehicle ignition interlock system 10 may also include a motion detector 80 that is configured to detect if the vehicle is moving. The motion detector 80 may be a GPS receiver, an accelerometer, a gyroscopic motion detector, or any other device capable of detection vehicle motion. The vehicle ignition interlock system controller 34 communicates with the motion detector 80 and can be configured to provide a message to the vehicle operator in response to detecting movement of the vehicle when the breath alcohol level of the operator has not been measured prior to movement of the vehicle, especially when a vehicle start was not allowed.

According to embodiments of the present invention where the motion detector is a GPS device, the controller may also log vehicle geographic locations periodically, or when breath analyzer tests and/or retests are required.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

The invention claimed is:

1. A vehicle ignition interlock system, comprising:
   a breath analyzer located within a vehicle, wherein the breath analyzer comprises first and second alcohol sensors, each configured to detect breath alcohol levels of an operator of the vehicle, wherein the second alcohol sensor is a backup for the first alcohol sensor and becomes operational if the first alcohol sensor malfunctions; and
   a controller operably connected to the first and second alcohol sensors and to an ignition system of the vehicle, wherein the controller is configured to compare breath alcohol levels of the vehicle operator, as detected by either of the first or second alcohol sensor, with a threshold value, wherein the controller is configured to prevent vehicle ignition if a breath alcohol level detected by the breath analyzer is greater than or equal to the threshold value.

2. The vehicle ignition interlock system of claim 1, wherein the first and second alcohol sensors are selected from the group consisting of fuel cell sensors, infrared sensors, and metal oxide semiconductor sensors.

3. The vehicle ignition interlock system of claim 1, further comprising a user interface operably connected to the controller, wherein the controller displays operational messages via the user interface.

4. The vehicle ignition interlock system of claim 1, further comprising a user interface operably connected to the controller, wherein the controller provides audible operational messages and prompts via the user interface.

5. The vehicle ignition interlock system of claim 4, wherein the controller provides voice messages in one or more languages via the user interface.

6. The vehicle ignition interlock system of claim 1, further comprising a user selectable option that allows an individual to perform a breath alcohol test via the breath analyzer without enabling the vehicle ignition system.

7. The vehicle ignition interlock system of claim 1, further comprising an operator identification device operably connected to the controller, wherein the controller is configured to verify the identity of the vehicle operator via the operator identification device.

8. The vehicle ignition interlock system of claim 7, wherein the operator identification device comprises a fingerprint identification device.

9. A vehicle ignition interlock system, comprising:
   a breath analyzer located within a vehicle, wherein the breath analyzer comprises first and second alcohol sensors, each configured to detect breath alcohol levels of an operator of the vehicle, wherein the second alcohol sensor is a backup for the first alcohol sensor and becomes operational if the first alcohol sensor malfunctions, and wherein at least one of the first and second alcohol sensors is a mouth contamination sensor that is configured to distinguish between contaminants in the mouth of a vehicle operator and alcohol contained within a deep lung breath sample; and
   a controller operably connected to the first and second alcohol sensors and to an ignition system of the vehicle, wherein the controller is configured to compare breath alcohol levels of the vehicle operator, as detected by either of the first or second alcohol sensor, with a threshold value, wherein the controller is configured to prevent vehicle ignition if a breath alcohol level detected by the breath analyzer is greater than or equal to the threshold value.

10. The vehicle ignition interlock system of claim 9, wherein the first and second alcohol sensors are selected from the group consisting of fuel cell sensors, infrared sensors, and metal oxide semiconductor sensors.

11. The vehicle ignition interlock system of claim 9, wherein the controller is configured to trigger a breath alcohol retest of the vehicle operator via the breath analyzer in response to detecting the presence of a contaminant within the mouth of the vehicle operator.

12. The vehicle ignition interlock system of claim 9, wherein the mouth contamination sensor comprises a metal oxide semiconductor sensor.

13. The vehicle ignition interlock system of claim 12, wherein the mouth contamination sensor comprises a Taguchi sensor.

14. The vehicle ignition interlock system of claim 9, wherein the mouth contamination sensor comprises an infrared sensor.

15. The vehicle ignition interlock system of claim 9, wherein the controller is configured to require periodic breath alcohol tests of the vehicle operator via the breath analyzer, and wherein the controller is configured to increase the frequency of the periodic breath alcohol tests of the vehicle operator via the breath analyzer in response to detecting the presence of a contaminant within the mouth of the vehicle operator.

16. The vehicle ignition interlock system of claim 9, further comprising a user interface operably connected to the controller, wherein the controller displays operational messages via the user interface.

17. A vehicle ignition interlock system, comprising:
   a breath analyzer located within a vehicle, wherein the breath analyzer comprises first and second alcohol sensors, each configured to detect breath alcohol levels of an operator of the vehicle, wherein the first alcohol sensor is a fuel cell sensor, wherein the second alcohol sensor is a metal oxide semiconductor sensor, wherein the second alcohol sensor is a backup for the first alcohol sensor and becomes operational if the first alcohol sensor malfunctions, and wherein at least one of the first and second alcohol sensors is a mouth contamination sensor that is configured to distinguish between contaminants in the mouth of a vehicle operator and alcohol contained within a deep lung breath sample; and
   a controller operably connected to the first and second alcohol sensors and to an ignition system of the vehicle, wherein the controller is configured to compare breath alcohol levels of the vehicle operator, as detected by either of the first or second alcohol sensor, with a threshold value, wherein the controller is configured to prevent vehicle ignition if a breath alcohol level detected by the breath analyzer is greater than or equal to the threshold value, wherein the controller is configured to require periodic breath alcohol tests of the vehicle operator via the breath analyzer, and wherein the controller is configured to increase the frequency of the periodic breath alcohol tests of the vehicle operator via the breath analyzer in response to detecting the presence of a contaminant within the mouth of the vehicle operator.

18. The vehicle ignition interlock system of claim 17, wherein the second alcohol sensor comprises a Taguchi sensor.

19. The vehicle ignition interlock system of claim 17, wherein the controller is configured to trigger a breath alcohol retest of the vehicle operator via the breath analyzer in response to detecting the presence of a contaminant within the mouth of the vehicle operator.

20. The vehicle ignition interlock system of claim 17, further comprising a user interface operably connected to the controller, wherein the controller displays operational messages via the user interface.

21. A vehicle ignition interlock system, comprising:
   a breath analyzer located within a vehicle, wherein the breath analyzer is configured to detect breath alcohol levels of an operator of the vehicle;
   an impact sensor that is configured to detect impact events experienced by one or more portions of the vehicle ignition interlock system;
   a controller operably connected to the breath analyzer, to the impact sensor, and to an ignition system of the vehicle, wherein the controller is configured to compare detected breath alcohol levels of the vehicle operator with a threshold value, wherein the controller is configured to prevent vehicle ignition if a breath alcohol level detected by the breath analyzer is greater than or equal to the threshold value, and wherein the controller is configured to record impact events detected by the impact sensor.

22. The vehicle ignition interlock system of claim 21, wherein the controller is configured to provide a message to the vehicle operator in response to the impact sensor detecting an impact event.

23. The vehicle ignition interlock system of claim 22, further comprising a user interface operably connected to the controller, and wherein the controller provides a message to the vehicle operator via the user interface in response to the impact sensor detecting an impact event.

24. The vehicle ignition interlock system of claim 22, wherein the message is an audio message.

25. The vehicle ignition interlock system of claim 24, wherein the controller provides the audio message comprises a voice message in one or more languages.

26. The vehicle ignition interlock system of claim 21, wherein the impact sensor comprises an accelerometer.

27. The vehicle ignition interlock system of claim 21, further comprising a motion detector in communication with the controller, wherein the motion detector is configured to detect vehicle motion.

28. The vehicle ignition interlock system of claim 27, wherein the motion detector is selected from the group consisting of GPS devices, accelerometers, and gyroscopic motion sensors.

29. A vehicle ignition interlock system, comprising:
- a breath analyzer located within a vehicle, wherein the breath analyzer is configured to detect breath alcohol levels of an operator of the vehicle;
- a motion detector device configured to detect vehicle motion;
- a controller operably connected to the breath analyzer, to the motion detector device, and to an ignition system of the vehicle, wherein the controller is configured to compare detected breath alcohol levels of the vehicle operator with a threshold value, wherein the controller is configured to prevent vehicle ignition if a breath alcohol level detected by the breath analyzer is greater than or equal to the threshold value.

30. The vehicle ignition interlock system of claim 29, wherein the controller is configured to provide a message to the vehicle operator in response to detecting movement of the vehicle via the motion detector device and to detecting that the breath alcohol level of the operator has not been measured within a predetermined period of time.

31. The vehicle ignition interlock system of claim 30, further comprising a user interface operably connected to the controller, and wherein the controller provides a message to the vehicle operator via the user interface in response to detecting movement of the vehicle via the motion detector device.

32. The vehicle ignition interlock system of claim 30, wherein the message is an audio message.

33. The vehicle ignition interlock system of claim 32, wherein the controller provides the audio message comprises a voice message in one or more languages.

34. The vehicle ignition interlock system of claim 29, wherein the motion detector is selected from the group consisting of GPS devices, accelerometers, and gyroscopic motion sensors.

* * * * *